(12) United States Patent
Andino

(10) Patent No.: US 9,962,524 B2
(45) Date of Patent: May 8, 2018

(54) MEDICAL ARTICLE SECUREMENT DEVICE

(75) Inventor: Rafael V. Andino, Grayson, GA (US)

(73) Assignee: Venetec International, Inc., Murray Hill, NJ (US)

( * ) Notice: Subject to any disclaimer, the term of this patent is extended or adjusted under 35 U.S.C. 154(b) by 1802 days.

(21) Appl. No.: 13/415,644

(22) Filed: Mar. 8, 2012

(65) Prior Publication Data
US 2012/0232490 A1  Sep. 13, 2012

Related U.S. Application Data

(60) Provisional application No. 61/452,014, filed on Mar. 11, 2011.

(51) Int. Cl.
*A61M 25/02* (2006.01)

(52) U.S. Cl.
CPC ....... *A61M 25/02* (2013.01); *A61M 2025/028* (2013.01); *A61M 2025/0266* (2013.01)

(58) Field of Classification Search
CPC .......... A61M 5/14244; A61M 5/14248; A61M 25/0014; A61M 25/02; A61M 2025/0253; A61M 2025/0266; A61M 2025/028
USPC .... 604/93.01, 174, 180, 500, 506, 507, 508, 604/513
See application file for complete search history.

(56) References Cited

U.S. PATENT DOCUMENTS

| | | | |
|---|---|---|---|
| 2,402,306 A | 6/1946 | Turkel | |
| 2,525,398 A | 10/1950 | Collins | |
| 2,533,961 A | 12/1950 | Rousseau et al. | |
| 3,046,984 A | 7/1962 | Eby | |
| 3,064,648 A | 11/1962 | Bujan | |
| 3,167,072 A | 1/1965 | Stone et al. | |
| 3,194,235 A | 7/1965 | Cooke | |
| 3,245,567 A | 4/1966 | Knight | |
| 3,288,137 A | 11/1966 | Lund | |
| 3,394,954 A | 7/1968 | Sarns | |
| 3,493,238 A | 2/1970 | Ludwig | |
| 3,529,597 A | 9/1970 | Fuzak | |
| 3,589,361 A | 6/1971 | Loper et al. | |
| 3,630,195 A | 12/1971 | Santomieri | |
| 3,677,250 A | 7/1972 | Thomas | |
| 3,686,896 A | 8/1972 | Rutter | |
| 3,766,915 A | 10/1973 | Rychlik | |

(Continued)

FOREIGN PATENT DOCUMENTS

| CA | 1311977 C | 12/1992 |
|---|---|---|
| CA | 1318824 C | 6/1993 |

(Continued)

OTHER PUBLICATIONS

"Definition of Battery." Oxford Dictionaries. http://www.oxford-dictionaries.com/us/definition/american_english/battery.*

(Continued)

*Primary Examiner* — Aarti B Berdichevsky
(74) *Attorney, Agent, or Firm* — Rutan & Tucker, LLP

(57) ABSTRACT

A securement system includes a securement device which permits various medical articles, for example, an indwelling catheter and one or more medical lines, to be fluidly connected to one another. The securement device can be releasably secured relative to an anchor pad which itself is secured to a patient. In this way, the securement system can secure an interconnection of medical articles relative to a patient.

25 Claims, 8 Drawing Sheets

(56) References Cited

U.S. PATENT DOCUMENTS

| | | |
|---|---|---|
| 3,812,851 A | 5/1974 | Rodriguez |
| 3,817,240 A | 6/1974 | Ayres |
| 3,826,254 A | 7/1974 | Mellor |
| 3,834,380 A | 9/1974 | Boyd |
| 3,856,020 A | 12/1974 | Kovac |
| 3,863,631 A | 2/1975 | Baldwin |
| 3,900,026 A | 8/1975 | Wagner |
| 3,901,226 A | 8/1975 | Scardenzan |
| 3,906,946 A | 9/1975 | Nordstrom |
| 3,920,001 A | 11/1975 | Edwards |
| 3,934,576 A | 1/1976 | Danielsson |
| 3,942,228 A | 3/1976 | Buckman et al. |
| 3,973,565 A | 8/1976 | Steer |
| 4,004,586 A | 1/1977 | Christensen et al. |
| D243,477 S | 2/1977 | Cutruzzula et al. |
| 4,020,835 A | 5/1977 | Nordstrom et al. |
| 4,037,599 A | 7/1977 | Raulerson |
| 4,059,105 A | 11/1977 | Cutruzzula et al. |
| 4,079,738 A | 3/1978 | Dunn et al. |
| 4,082,094 A | 4/1978 | Dailey |
| 4,114,618 A | 9/1978 | Vargas |
| 4,116,196 A | 9/1978 | Kaplan et al. |
| 4,123,091 A | 10/1978 | Cosentino et al. |
| 4,129,128 A | 12/1978 | McFarlane |
| 4,133,312 A | 1/1979 | Burd |
| 4,142,527 A | 3/1979 | Garcia |
| 4,161,177 A | 7/1979 | Fuchs |
| D252,822 S | 9/1979 | McFarlane |
| 4,170,993 A | 10/1979 | Alvarez |
| 4,193,174 A | 3/1980 | Stephens |
| 4,194,504 A | 3/1980 | Harms et al. |
| D256,162 S | 7/1980 | Haerr et al. |
| 4,224,937 A | 9/1980 | Gordon |
| 4,230,109 A | 10/1980 | Geiss |
| 4,250,880 A | 2/1981 | Gordon |
| 4,275,721 A | 6/1981 | Olson |
| 4,314,568 A | 2/1982 | Loving |
| 4,316,461 A | 2/1982 | Marais et al. |
| 4,324,236 A | 4/1982 | Gordon et al. |
| 4,326,519 A | 4/1982 | D'Alo et al. |
| 4,333,468 A | 6/1982 | Geist |
| 4,362,156 A | 12/1982 | Feller, Jr. et al. |
| 4,392,853 A | 7/1983 | Muto |
| 4,397,647 A | 8/1983 | Gordon |
| 4,398,757 A | 8/1983 | Floyd et al. |
| 4,405,163 A | 9/1983 | Voges et al. |
| 4,405,312 A | 9/1983 | Gross et al. |
| 4,435,174 A | 3/1984 | Redmond et al. |
| 4,435,175 A | 3/1984 | Friden |
| 4,439,193 A | 3/1984 | Larkin |
| D273,993 S | 5/1984 | Schulte et al. |
| 4,449,975 A | 5/1984 | Perry |
| 4,453,933 A | 6/1984 | Speaker |
| 4,470,410 A | 9/1984 | Elliott |
| 4,474,559 A | 10/1984 | Steiger |
| 4,480,639 A | 11/1984 | Peterson et al. |
| 4,484,913 A | 11/1984 | Swauger |
| 4,516,968 A | 5/1985 | Marshall et al. |
| 4,517,971 A | 5/1985 | Sorbonne |
| 4,561,857 A | 12/1985 | Sacks |
| 4,563,177 A | 1/1986 | Kamen |
| 4,585,435 A | 4/1986 | Vaillancourt |
| 4,585,444 A | 4/1986 | Harris |
| 4,631,056 A | 12/1986 | Dye |
| 4,632,670 A | 12/1986 | Mueller, Jr. |
| 4,633,863 A | 1/1987 | Filips et al. |
| 4,645,492 A | 2/1987 | Weeks |
| 4,650,473 A | 3/1987 | Bartholomew et al. |
| 4,660,555 A | 4/1987 | Payton |
| 4,666,434 A | 5/1987 | Kaufman |
| 4,669,458 A | 6/1987 | Abraham et al. |
| 4,693,710 A | 9/1987 | McCool |
| 4,711,636 A | 12/1987 | Bierman |
| 4,723,948 A | 2/1988 | Clark et al. |
| 4,737,143 A | 4/1988 | Russell |
| 4,742,824 A | 5/1988 | Payton et al. |
| 4,743,231 A | 5/1988 | Kay et al. |
| 4,752,292 A | 6/1988 | Lopez et al. |
| 4,792,163 A | 12/1988 | Kulle |
| 4,795,429 A | 1/1989 | Feldstein |
| 4,826,486 A | 5/1989 | Palsrok et al. |
| 4,834,702 A | 5/1989 | Rocco |
| 4,834,716 A | 5/1989 | Ogle, II |
| 4,838,858 A | 6/1989 | Wortham et al. |
| D302,304 S | 7/1989 | Kulle et al. |
| 4,846,807 A | 7/1989 | Safadago |
| 4,852,844 A | 8/1989 | Villaveces |
| 4,857,058 A | 8/1989 | Payton |
| 4,863,432 A | 9/1989 | Kvalo |
| 4,878,897 A | 11/1989 | Katzin |
| 4,880,412 A | 11/1989 | Weiss |
| 4,895,570 A | 1/1990 | Larkin |
| 4,897,082 A | 1/1990 | Erskine |
| 4,898,587 A | 2/1990 | Mera |
| 4,919,654 A | 4/1990 | Kalt |
| 4,934,375 A | 6/1990 | Cole et al. |
| 4,941,882 A | 7/1990 | Ward et al. |
| 4,955,864 A | 9/1990 | Hajduch |
| 4,966,582 A | 10/1990 | Sit et al. |
| 4,976,698 A | 12/1990 | Stokley |
| 4,976,700 A | 12/1990 | Tollini |
| 4,981,469 A | 1/1991 | Whitehouse et al. |
| 4,981,475 A | 1/1991 | Haindl |
| 4,997,421 A | 3/1991 | Palsrok et al. |
| 5,024,665 A | 6/1991 | Kaufman |
| 5,037,397 A | 8/1991 | Kalt et al. |
| 5,037,398 A | 8/1991 | Buchanan |
| 5,037,405 A | 8/1991 | Crosby |
| 5,074,847 A | 12/1991 | Greenwell et al. |
| D323,390 S | 1/1992 | Paine et al. |
| 5,084,026 A | 1/1992 | Shapiro |
| 5,098,048 A | 3/1992 | Chen |
| 5,105,807 A | 4/1992 | Kahn et al. |
| 5,112,313 A | 5/1992 | Sallee |
| 5,116,324 A | 5/1992 | Brierley et al. |
| 5,120,320 A | 6/1992 | Fayngold |
| 5,135,506 A | 8/1992 | Gentelia et al. |
| 5,137,519 A | 8/1992 | Littrell et al. |
| 5,147,322 A | 9/1992 | Bowen et al. |
| 5,156,641 A | 10/1992 | White |
| 5,163,913 A | 11/1992 | Rantanen-Lee et al. |
| 5,167,630 A | 12/1992 | Paul |
| 5,192,273 A | 3/1993 | Bierman et al. |
| 5,192,274 A | 3/1993 | Bierman |
| 5,195,981 A | 3/1993 | Johnson |
| 5,215,532 A | 6/1993 | Atkinson |
| 5,238,010 A | 8/1993 | Grabenkort et al. |
| 5,248,306 A | 9/1993 | Clark et al. |
| 5,263,943 A | 11/1993 | Vanderbrook |
| 5,267,967 A | 12/1993 | Schneider |
| 5,290,248 A | 3/1994 | Bierman |
| 5,306,253 A | 4/1994 | Brimhall |
| 5,306,256 A | 4/1994 | Jose |
| D347,060 S | 5/1994 | Bierman |
| 5,314,411 A | 5/1994 | Bierman et al. |
| 5,328,487 A | 7/1994 | Starchevich |
| 5,330,438 A | 7/1994 | Gollobin et al. |
| 5,336,195 A | 8/1994 | Daneshvar |
| 5,341,411 A | 8/1994 | Hashimoto |
| 5,344,414 A | 9/1994 | Lopez et al. |
| 5,354,282 A | 10/1994 | Bierman |
| 5,356,379 A | 10/1994 | Vaillancourt |
| 5,356,391 A | 10/1994 | Stewart |
| 5,370,627 A | 12/1994 | Conway |
| 5,380,293 A | 1/1995 | Grant |
| 5,380,294 A | 1/1995 | Persson |
| 5,380,301 A | 1/1995 | Prichard et al. |
| 5,382,239 A | 1/1995 | Orr et al. |
| 5,382,240 A | 1/1995 | Lam |
| 5,395,344 A | 3/1995 | Beisang, III et al. |
| 5,413,120 A | 5/1995 | Grant |
| 5,413,562 A | 5/1995 | Swauger |
| D359,120 S | 6/1995 | Sallee et al. |
| 5,456,671 A | 10/1995 | Bierman |

(56) References Cited

U.S. PATENT DOCUMENTS

| | | | |
|---|---|---|---|
| 5,470,321 A | 11/1995 | Forster et al. |
| D364,922 S | 12/1995 | Bierman |
| 5,484,425 A | 1/1996 | Fischell et al. |
| 5,496,283 A | 3/1996 | Alexander |
| 5,507,535 A | 4/1996 | McKamey et al. |
| 5,531,695 A | 7/1996 | Swisher |
| D375,355 S | 11/1996 | Bierman |
| D375,356 S | 11/1996 | Bierman |
| 5,577,516 A | 11/1996 | Schaeffer |
| 5,578,013 A | 11/1996 | Bierman |
| D377,831 S | 2/1997 | Bierman |
| 5,605,546 A | 2/1997 | Wolzinger et al. |
| 5,620,427 A | 4/1997 | Werschmidt et al. |
| 5,626,565 A | 5/1997 | Landis et al. |
| 5,643,217 A | 7/1997 | Dobkin |
| 5,681,290 A | 7/1997 | Alexander |
| 5,664,581 A | 9/1997 | Ashley |
| 5,685,859 A | 11/1997 | Kornerup |
| 5,686,096 A | 11/1997 | Khan et al. |
| 5,690,616 A | 11/1997 | Mogg |
| 5,690,617 A | 11/1997 | Wright |
| 5,693,032 A | 12/1997 | Bierman |
| 5,702,371 A | 12/1997 | Bierman |
| 5,722,959 A | 3/1998 | Bierman |
| 5,728,053 A | 3/1998 | Calvert |
| 5,755,225 A | 5/1998 | Hutson |
| 5,800,402 A | 9/1998 | Bierman |
| 5,800,410 A | 9/1998 | Gawreluk |
| 5,810,781 A | 9/1998 | Bierman |
| 5,814,021 A | 9/1998 | Balbierz |
| D399,954 S | 10/1998 | Bierman |
| 5,827,230 A | 10/1998 | Bierman |
| 5,827,239 A | 10/1998 | Dillon et al. |
| 5,833,666 A | 11/1998 | Davis et al. |
| 5,833,667 A | 11/1998 | Bierman |
| 5,855,591 A | 1/1999 | Bierman |
| 5,885,251 A | 3/1999 | Luther |
| 5,885,254 A | 3/1999 | Matyas |
| 5,897,519 A | 4/1999 | Shesol et al. |
| 5,947,931 A | 9/1999 | Bierman |
| 6,050,934 A | 4/2000 | Mikhail et al. |
| D425,619 S | 5/2000 | Bierman |
| 6,099,509 A | 8/2000 | Brown, Jr. et al. |
| 6,113,577 A | 9/2000 | Hakky et al. |
| 6,132,398 A | 10/2000 | Bierman |
| 6,132,399 A | 10/2000 | Shultz |
| 6,139,532 A | 10/2000 | Howell et al. |
| D433,503 S | 11/2000 | Powers et al. |
| 6,213,979 B1 | 4/2001 | Bierman |
| 6,213,996 B1 | 4/2001 | Jepson et al. |
| 6,224,571 B1 | 5/2001 | Bierman |
| 6,228,064 B1 | 5/2001 | Abita et al. |
| 6,231,547 B1 | 5/2001 | O'Hara |
| 6,231,548 B1 | 5/2001 | Bassett |
| 6,258,066 B1 | 7/2001 | Urich |
| 6,270,086 B1 | 8/2001 | Lloyd |
| 6,283,945 B1 | 9/2001 | Bierman |
| 6,290,676 B1 | 9/2001 | Bierman |
| 6,332,874 B1 | 12/2001 | Eliasen et al. |
| 6,361,523 B1 | 3/2002 | Bierman |
| 6,375,639 B1 | 4/2002 | Duplessie et al. |
| 6,413,240 B1 | 7/2002 | Bierman et al. |
| 6,428,515 B1 | 8/2002 | Bierman et al. |
| 6,428,516 B1 | 8/2002 | Bierman |
| 6,436,073 B1 | 8/2002 | Von Teichert |
| 6,447,485 B2 | 9/2002 | Bierman |
| 6,447,486 B1 | 9/2002 | Tollini |
| 6,471,676 B1 | 10/2002 | DeLegge et al. |
| 6,482,183 B1 | 11/2002 | Pausch et al. |
| 6,491,664 B2 | 12/2002 | Bierman |
| 6,500,154 B1 | 12/2002 | Hakky et al. |
| D469,530 S | 1/2003 | Gomez |
| D470,936 S | 2/2003 | Bierman |
| 6,517,522 B1 | 2/2003 | Bell et al. |
| 6,551,285 B1 | 4/2003 | Bierman |
| 6,572,588 B1 | 6/2003 | Bierman et al. |
| 6,582,403 B1 | 6/2003 | Bierman et al. |
| 6,616,635 B1 | 9/2003 | Bell et al. |
| 6,626,890 B2 | 9/2003 | Nguyen et al. |
| 6,652,487 B1 | 11/2003 | Cook |
| 6,663,600 B2 | 12/2003 | Bierman et al. |
| 6,673,046 B2 | 1/2004 | Bierman et al. |
| 6,689,104 B2 | 2/2004 | Bierman |
| D492,411 S | 6/2004 | Bierman |
| 6,770,055 B2 | 8/2004 | Bierman et al. |
| 6,786,892 B2 | 9/2004 | Bierman |
| 6,809,230 B2 | 10/2004 | Hancock et al. |
| 6,824,527 B2 | 11/2004 | Gollobin |
| 6,827,705 B2 | 12/2004 | Bierman |
| 6,827,706 B2 | 12/2004 | Tollini |
| 6,827,707 B2 | 12/2004 | Wright et al. |
| 6,834,652 B2 | 12/2004 | Altman |
| 6,837,875 B1 | 1/2005 | Bierman |
| 6,866,652 B2 | 3/2005 | Bierman |
| D503,977 S | 4/2005 | Bierman |
| 6,951,550 B2 | 10/2005 | Bierman |
| 6,972,003 B2 | 12/2005 | Bierman et al. |
| 6,979,320 B2 | 12/2005 | Bierman |
| 6,981,969 B2 | 1/2006 | Chavez et al. |
| 7,014,627 B2 | 3/2006 | Bierman |
| 7,018,362 B2 | 3/2006 | Bierman et al. |
| 7,070,580 B2 | 7/2006 | Nielsen |
| 7,090,660 B2 | 8/2006 | Roberts et al. |
| D528,206 S | 9/2006 | Bierman |
| 7,144,387 B2 | 12/2006 | Millerd |
| 7,153,291 B2 | 12/2006 | Bierman |
| 7,354,421 B2 | 4/2008 | Bierman |
| 7,491,190 B2 | 2/2009 | Bierman et al. |
| 7,935,083 B2 | 5/2011 | Bierman et al. |
| 2002/0068904 A1 | 6/2002 | Bierman et al. |
| 2002/0099360 A1 | 7/2002 | Bierman |
| 2002/0111601 A1* | 8/2002 | Thompson ............ 604/514 |
| 2002/0133121 A1 | 9/2002 | Bierman |
| 2003/0055382 A1 | 3/2003 | Schaeffer |
| 2003/0163096 A1 | 8/2003 | Swenson et al. |
| 2003/0181870 A1 | 9/2003 | Bressler et al. |
| 2003/0229313 A1 | 12/2003 | Bierman |
| 2004/0102736 A1 | 5/2004 | Bierman |
| 2004/0111067 A1 | 6/2004 | Kirchhofer |
| 2004/0204685 A1 | 10/2004 | Wright et al. |
| 2005/0096606 A1 | 5/2005 | Millerd |
| 2005/0182367 A1 | 8/2005 | Walborn |
| 2005/0215953 A1 | 9/2005 | Rossen |
| 2005/0288635 A1 | 12/2005 | Davis et al. |
| 2006/0015076 A1 | 1/2006 | Heinzerling et al. |
| 2006/0064063 A1 | 3/2006 | Bierman |
| 2006/0079740 A1 | 4/2006 | Silver et al. |
| 2006/0135944 A1 | 6/2006 | Bierman |
| 2006/0184127 A1 | 8/2006 | Bierman |
| 2006/0184129 A1 | 8/2006 | Bierman |
| 2006/0217669 A1 | 9/2006 | Botha |
| 2006/0247577 A1 | 11/2006 | Wright |
| 2006/0264836 A1 | 11/2006 | Bierman |
| 2006/0270994 A1* | 11/2006 | Bierman ............ 604/180 |
| 2006/0270995 A1 | 11/2006 | Bierman |
| 2007/0016166 A1 | 1/2007 | Thistle |
| 2007/0083153 A1* | 4/2007 | Haar ............ 604/67 |
| 2007/0250021 A1 | 10/2007 | Brimhall et al. |
| 2008/0045905 A1 | 2/2008 | Chawki |
| 2008/0300543 A1 | 12/2008 | Abriles et al. |
| 2010/0049139 A1 | 2/2010 | Kiyono et al. |
| 2010/0298777 A1* | 11/2010 | Nishtala ............ 604/174 |
| 2012/0265147 A1 | 10/2012 | Andino et al. |
| 2013/0079723 A1* | 3/2013 | Andino ............ G04F 1/005 604/180 |

FOREIGN PATENT DOCUMENTS

| | | |
|---|---|---|
| DE | 2 341 297 | 4/1975 |
| EP | 0 114 677 | 5/1989 |
| EP | 0 356 683 | 7/1989 |
| EP | 0 169 704 | 11/1989 |
| EP | 0 367 549 | 5/1990 |
| EP | 0 263 789 | 6/1991 |

(56) References Cited

FOREIGN PATENT DOCUMENTS

| EP | 0 247 590 | | 12/1993 |
|---|---|---|---|
| EP | 0 720 836 | | 7/1996 |
| FR | 2922458 | A1 | 4/2009 |
| GB | 2 063 679 | | 6/1981 |
| GB | 2 086 466 | | 5/1982 |
| GB | 2 178 811 | | 2/1987 |
| WO | WO 90/05559 | | 5/1990 |
| WO | 9421319 | A1 | 9/1994 |
| WO | 9715337 | A1 | 5/1997 |
| WO | 9955409 | A1 | 11/1999 |
| WO | 2004016309 | A2 | 2/2004 |
| WO | 09/032008 | A2 | 3/2009 |
| WO | 10/132837 | A1 | 11/2010 |

OTHER PUBLICATIONS

International Search Report from PCT/US2007/077302 dated Mar. 28, 2008.
National Patent Services, Search Report re Patent Validity Study of U.S. Pat. No. 5,827,230, pp. MDG 001319-MDG 001320, May 23, 2006.
Cravens, et al., Urinary Catheter Management, American Family Physician, vol. 61, No. 2, pp. MDG 000273-MDG 000282, Jan. 15, 2000.
Dale® Foley Catheter Holder brochure, pp. MDG 000344-MDG 000346, 2002.
Grip-LokTM Universal Tubing Securement brochure, pp. MDG 000348-MDG 000349, undated.
M.C. Johnson Co., Cath-Secure® brochure, pp. MDG 000357-MDG 000360, undated.
Grip-Lok Universal Tubing Securement brochure, pp. MDG 000364-MDG 000366, 2005-2006.
Expert Discusses Strategies to Prevent CAUTIs, Infection Control Today, pp. MDG 000603-MDG-000609, Jun. 2005.
U.S. Appl. No. 13/577,425, filed Sep. 17, 2012, Non-Final Office Action of dated May 21, 2015.
U.S. Appl. No. 13/577,425, filed Sep. 17, 2012, Final Office Action of dated Sep. 8, 2015.
U.S. Appl. No. 13/577,425, filed Sep. 17, 2012, Advisory Action of dated Dec. 4, 2015.
U.S. Appl. No. 13/498,121, filed Jul. 3, 2012 Final Office Action dated Nov. 5, 2015.
U.S. Appl. No. 13/320,381, filed Feb. 27, 2012 Non-Final Office Action dated Aug. 26, 2015.
U.S. Appl. No. 13/320,381, filed Feb. 27, 2012 Final Office Action dated Dec. 17, 2015.
PCT/US2011/026897 filed Mar. 2, 2011 International Search Report dated Apr. 26, 2011.
PCT/US2010/051664 filed Oct. 6, 2010 International Search Report and Written Opinion dated Dec. 2, 2010.
PCT/US2010/035004 filed May 14, 2010 International Search Report and Written Opinion dated Jul. 21, 2010.
AU 2010303477 filed Oct. 6, 2010 Examiner's Search Report dated Oct. 22, 2015.
U.S. Appl. No. 13/320,381, filed Feb. 27, 2012 Non-Final Office Action dated Jul. 29, 2016.
U.S. Appl. No. 13/498,121, filed Jul. 3, 2012 Non-Final Office Action dated Jun. 3, 2016.

\* cited by examiner

MEDICAL ARTICLE SECUREMENT DEVICE

CROSS-REFERENCE TO RELATED APPLICATIONS

This application claims priority under 35 U.S.C. § 119(e) to U.S. Provisional Patent Application Ser. No. 61/452,014, filed Mar. 11, 2011, and entitled MEDICAL ARTICLE SECUREMENT DEVICE, which is hereby expressly incorporated by reference in its entirety.

BACKGROUND OF THE INVENTION

Field of the Invention

This application relates in general to a securement device for a medical article. More particularly, the device disclosed herein can interconnect various medical articles with one another. Additionally, the device can releasably secure to a patient's skin.

Description of the Related Art

It is common in the treatment of patients to utilize catheters to introduce fluids and medications directly into the patient or to withdraw fluids from the patient. When introducing fluid into a patient, the fluid (e.g., parenteral liquid, medication, etc.) typically drains from a container positioned above the patient to feed under gravity or is delivered via an infusion pump. The fluid flows through a medical line and into, for example, an indwelling catheter inserted into the patient. The inserted medical article and medical line are often releasably secured to each other by a conventional T-connection.

A T-connection generally includes a male connector with a tapered conical portion that is adapted to fit into a correspondingly shaped receptacle of a female connector (i.e., a hub). A spin nut is commonly disposed on the male connector and is rotatable relative to the tapered conical portion. The spin nut includes internal threads adapted to engage external threads on the female connector to lock the connectors together. When properly engaged, the conical portion fits tightly within the receptacle to produce a sealed interconnection.

SUMMARY

The systems, devices, and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of Certain Embodiments," one will understand how the features of this invention provide several advantages over existing medical devices.

In one embodiment, a medical article securement system includes a retainer that has a first lumen defined between a first port and a second port, and a second lumen fluidly connected to the first lumen. The system further includes an anchor pad that has an upper surface and a lower surface. At least a portion of the lower surface is covered by adhesive. The system further comprises interengaging structure releasably securing the retainer to the anchor pad.

In another embodiment, a method of securing a medical article to a patient includes providing a retainer having a first lumen defined between a first port and a second port, and a second lumen fluidly connected to the first lumen. The method further includes providing an anchor pad having an upper surface and a lower surface. At least a portion of the lower surface is covered by adhesive. The method further includes releasably engaging the retainer to the anchor pad.

In yet another embodiment, a device for fluidly connecting a plurality of medical articles to an anchor includes a first lumen, a second lumen, a manifold connecting the first lumen to the second lumen, and at least one guiderail configured to slidably engage with the anchor.

BRIEF DESCRIPTION OF THE DRAWINGS

The above mentioned and other features of the invention will now be described with reference to the drawings of several embodiments of the present securement systems. The illustrated embodiments of the securement systems are intended to illustrate, but not to limit the invention. The drawings contain the following figures.

DETAILED DESCRIPTION OF CERTAIN EMBODIMENTS

The following description and examples illustrate certain embodiments of the present securement systems disclosed in the context of a catheterization system, and in particular in the context of a catheterization system utilizing a T-connector securement device. The catheterization system can include a catheter and one or more medical lines. More specifically, the embodiments relate to a securement system and related techniques that secure an interconnection of medical articles relative to a patient. Although, the embodiments of the securement systems are illustrated with intravenous catheters and medical lines, it will be understood by those of skill in the art in view of the present disclosure that the securement systems described herein can be used with other types of medical articles, including, but not limited to catheters and catheter hubs of various design, either with or without connectors or extension sets, such as central venous catheters, peripherally inserted central catheters, hemodialysis catheters, Foley catheters, as well as other designs of catheter hubs and catheter adaptors. Other medical articles may include surgical drainage tubes, feeding tubes, chest tubes, nasogastric tubes, rectal drains, external ventricular drains, chest tubes, any other sort of fluid supply or medical lines, connector fittings, and scopes, as well as electrical wires or cables connected to external or implanted electronic devices or sensors. The medical articles can each be a single medical article or a combination of medical articles.

One skilled in the art may also find additional applications for the devices, systems, and methods disclosed herein. Accordingly, the illustration and description of the securement systems in connection with a catheter and one or more medical lines is merely exemplary of one possible application of the securement systems and techniques disclosed.

The securement systems described with reference to the figures are especially adapted to arrest at least longitudinal movement of a medical article relative to an insertion site. The securement systems accomplish this without meaningfully impairing (i.e., substantially occluding) fluid flow through a lumen of the medical article or impairing insertion of a medical article, for example, a catheter. The securement systems may include retention mechanisms, for example, threaded fittings and male or female luer-lock connection fittings, to releasably secure one or more medical articles to the securement device.

Figure 1:
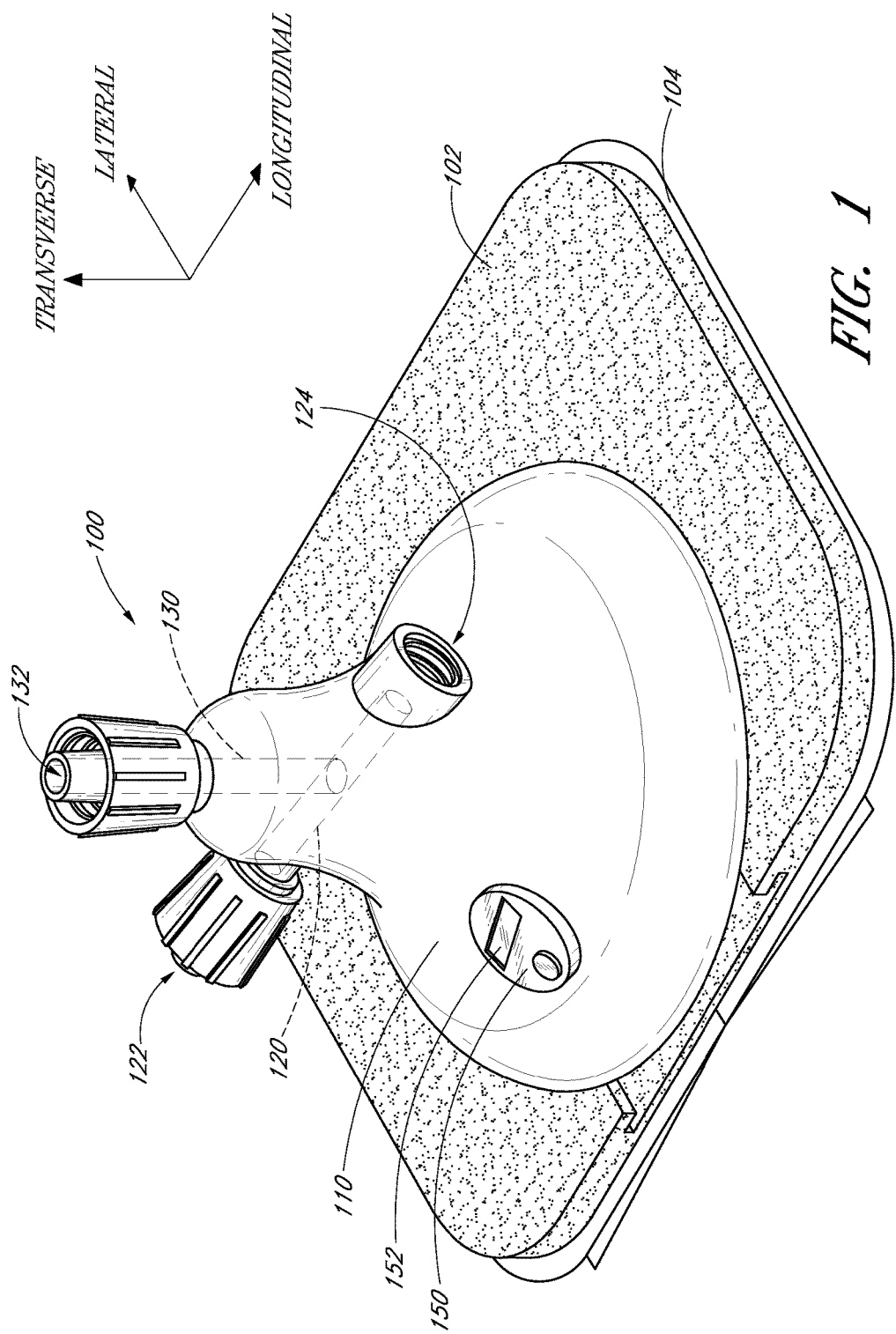
FIG. 1 is a perspective view of a securement system including an anchor pad and a securement device or retainer releasably secured thereto.

With reference now to FIG. 1, an embodiment of a securement system 100 includes an anchor pad 102 and a securement device or retainer 110. The securement device 110 may be fixed or releasable with the pad 102. For example, the securement device 110 illustrated in FIG. 1 is releasably secured to the anchor pad 102 via a channel 108 (see FIG. 2) extending in a lateral direction. Alternatively, the securement device 110 may be releasably secured to the anchor pad 102 in a transverse direction relative to the anchor pad with, for example, hook and loop fasteners.

The securement device 110 includes one or more channels 120. For embodiments that include two or more channels, the two channels may be interconnected within the securement device 110. For example, the illustrated securement device 110 includes a first channel 120 defining an internal lumen and a second channel 130 defining an internal lumen. The two lumens interconnect within the securement device 110. In this way, the securement device 110 fluidly interconnects two or more medical articles attached to the securement device 110. The first channel 120 includes an inlet port 122 and an outlet port 124. The second channel 130 includes an inlet port 132 at a first end and interconnects with the first channel 120 at a second end. In this way, the ports 122, 124, 132 are fluidly interconnected with one another. Each of the channels 110, 120 may have additional inlet and outlet ports depending on factors including the number of medical articles, desired flow arrangement through the securement device 110, the intended application of the securement device 110, and desired mixing of fluids through the securement device 110.

The anchor pad 102 is configured to be secured to a patient's skin and can include a release liner 104 disposed over an adhesive layer 106. As will be described in further detail below, in this way, medical articles can be interconnected with one another via the securement device 110 with the assembled securement device and medical articles being releasable from the anchor pad 102.

To assist in the description of the components of embodiments of the securement systems, the following coordinate terms are used, consistent with the coordinate axes illustrated in FIG. 1. A "longitudinal axis" is generally parallel to the first channel 120 of the securement device 110. A "lateral axis" is normal to the longitudinal axis and is generally parallel to the plane of the anchor pad 102. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The terms "proximal" and "distal" are used in reference to the center of the patient's body, as will be understood by one of skill in the art.

Anchor Pad

Figure 2:
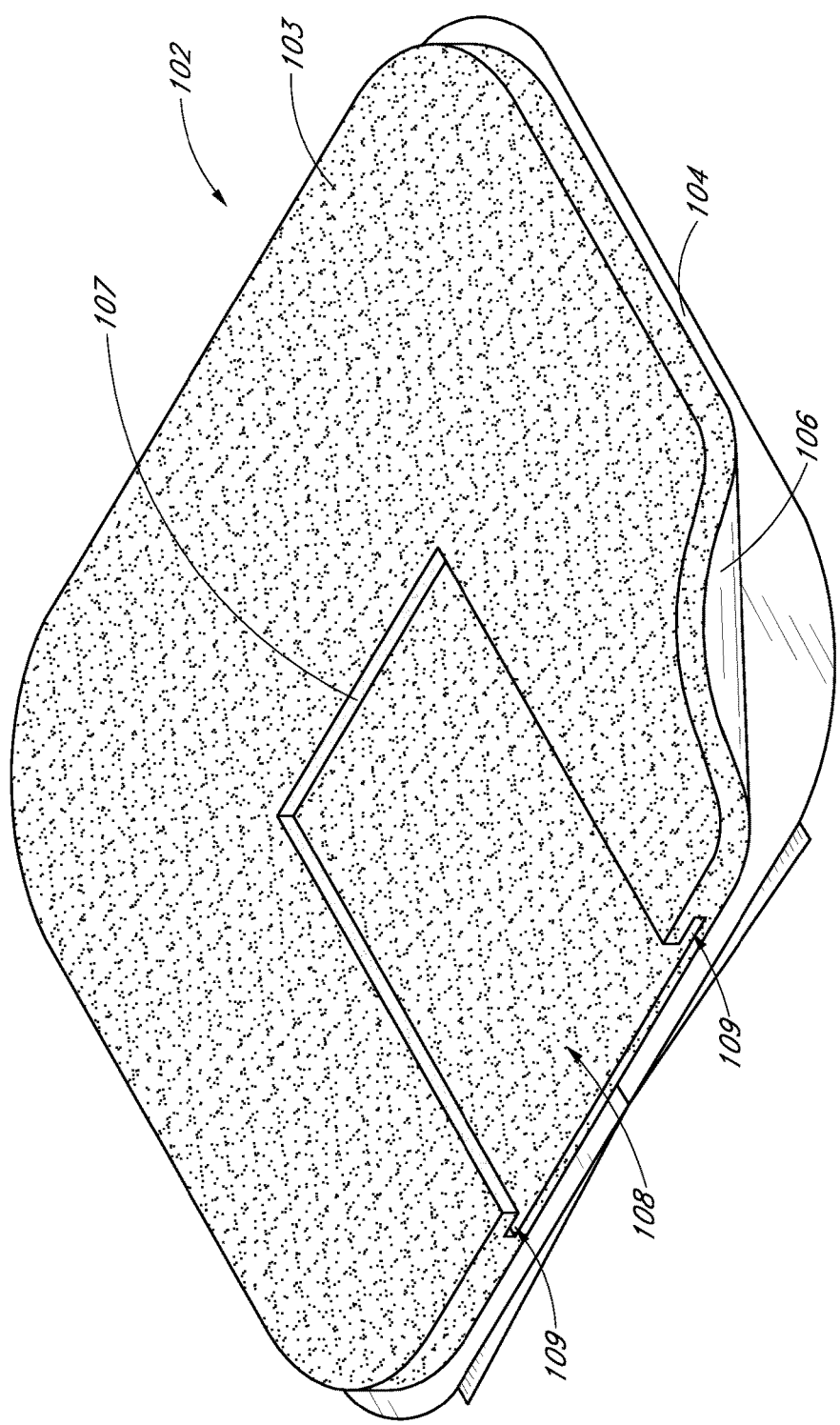
FIG. 2 is a perspective view of the anchor pad from FIG. 1 with the securement device removed.
Figure 3:
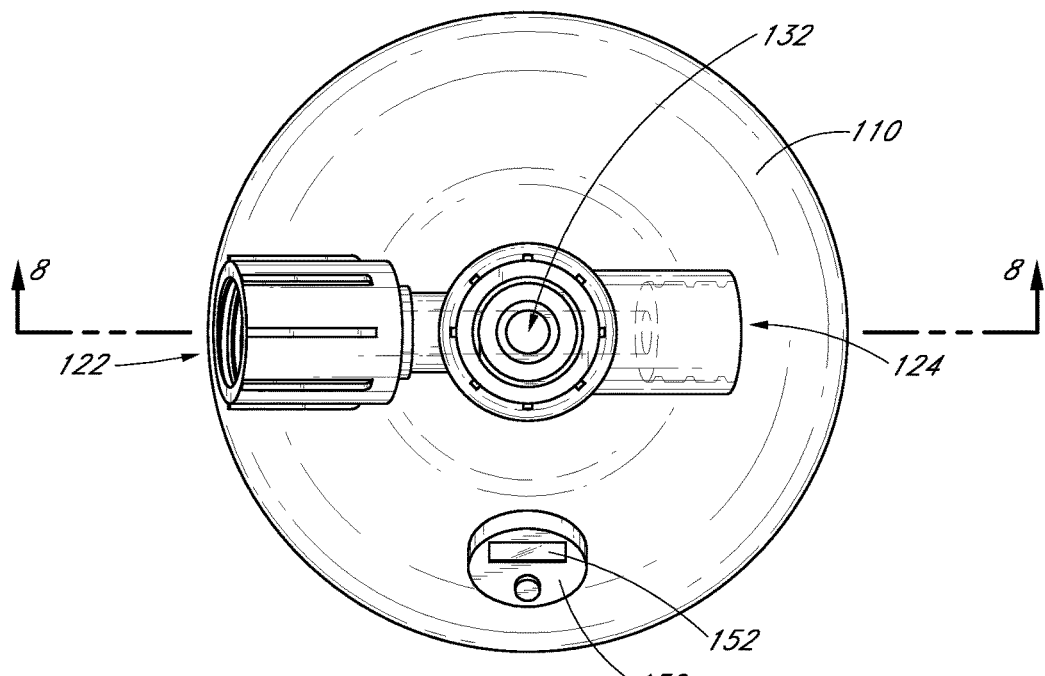
FIG. 3 is a top plan view of the securement device of FIG. 1 separate from the anchor pad.
Figure 9:
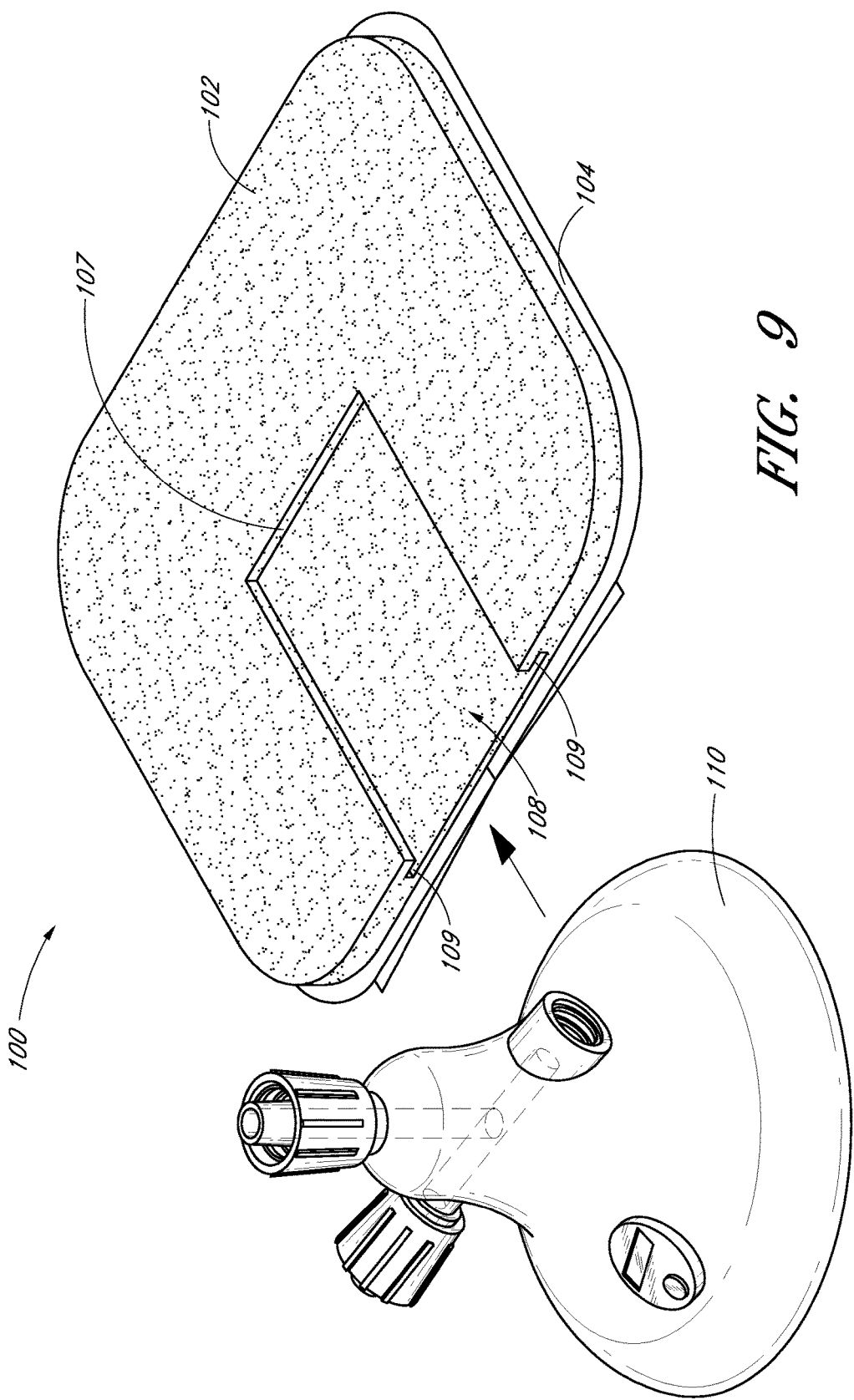
FIG. 9 is an exploded perspective view of the securement system showing the securement device aligned with the anchor pad of FIG. 1 prior to engaging the securement device with the anchor pad.
Figure 10:
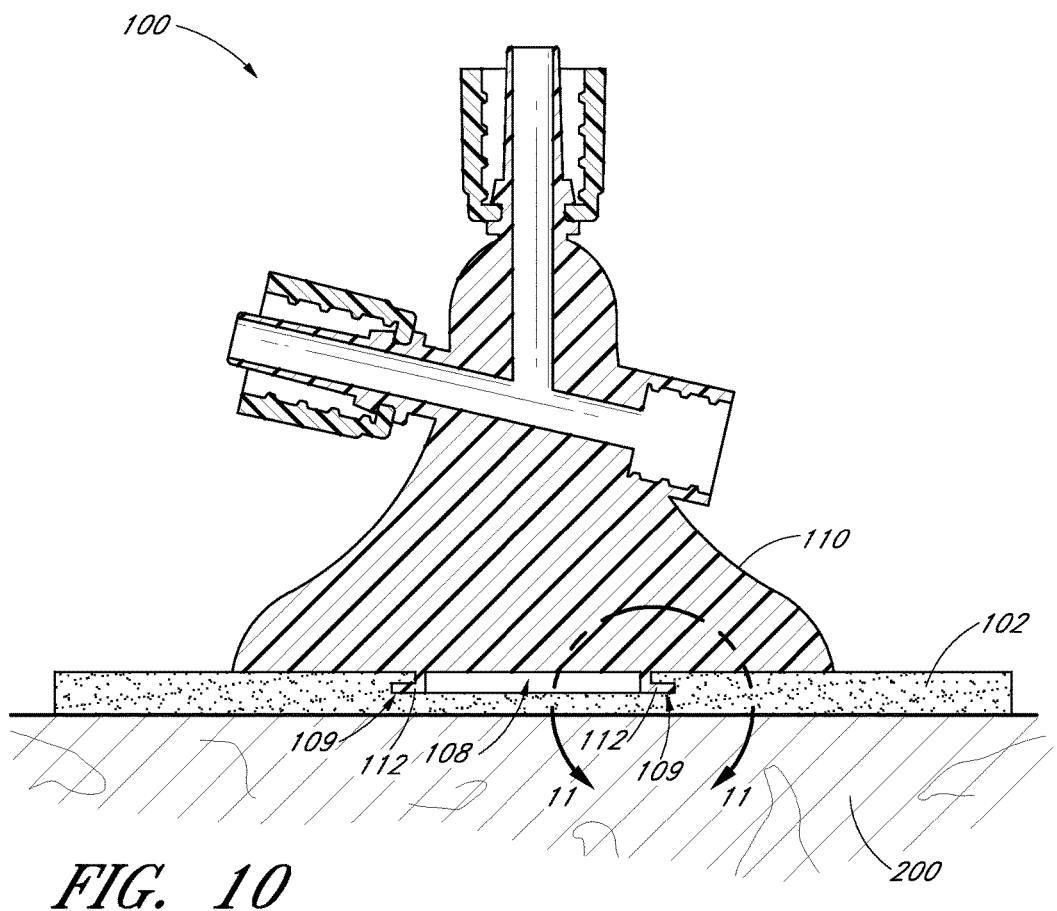
FIG. 10 is a cross-sectional view of the securement system of FIG. 1 with the anchor pad attached to the skin of a patient.

As can be seen in FIG. 2, the anchor pad 102 includes a releasable engagement structure for engaging with the securement device 110. Releasable engagement structures include hook and loop fasteners, grooves, channels, keyway, or other attachment structures known to a person having ordinary skill in the art. The engagement structure of the anchor pad 102 illustrated in FIG. 2 is a recess or channel 108. The channel 108 is disposed in an upper surface 103 of the pad 102 to receive and engage at least a portion of the securement device 110. As discussed in more detail below with reference to FIGS. 9-11, the channel 108 can include one or more grooves 109 to slidingly receive at least a portion of the securement device 110. For example, the anchor pad 102 can include two grooves 109 disposed on opposite sides of the channel 108 for receiving guiderails on the securement device 110. In this way, the guiderails of the securement device 110 slidingly engage the grooves 109 of the channel 108.

In some embodiments, the channel 108 extends from a first lateral side of the anchor pad 102 and terminates before reaching the second lateral side of the anchor pad 102. In such embodiments, the channel 108 forms an abutment surface 107 which prevents further lateral movement of the securement device 110 once the securement device 110 abuts against the surface 107. In other embodiments, the channel 108 extends through the anchor pad 102 from one lateral side to the other. Those of skill in the art will appreciate that the channel 108 can be oriented differently with respect to the coordinate axes of the securement system 100. For example, the channel 108 can extend longitudinally or at an angle relative to the longitudinal and lateral axes of the anchor pad 102.

The size and shape of the anchor pad 102 can vary depending on where the anchor pad 102 is intended to be positioned on a patient. For example, in some embodiments the securement system 100 may be intended for placement on a patient's hand and in other embodiments, the securement system 100 may be intended for placement on a different part of a patient, for example, a patient's back. The anchor pad 102 may be any size or shape that allows attachment of the anchor pad 102 to a patient's skin and that is configured to support at least the securement device 110. In the illustrated embodiment, the size and shape of the anchor pad 102 is selected to support at least two medical lines and a catheter. In some embodiments, the anchor pad 102 is configured to support more than two medical lines and/or additional medical articles, for example, two extension sets and two medical lines. In such an embodiment, the size and shape of the anchor pad 103 may be increased to provide support for the additional medical line.

The anchor pad 102 has a lower adhesive surface 106 for adhering to the skin of a patient and an upper surface 103. The anchor pad 102 is configured to support at least the securement device 110, as described above. In combination, the lower adhesive surface 106, the upper surface 103, and possibly one or more intermediate layers may comprise a laminate structure. A suitable laminate that comprises a foam or woven material with an adhesive layer is available commercially from Avery Dennison of Painsville, Ohio. The anchor pad 102 may be configured as a flexible structure which conforms to the surface of a patient's skin.

The lower adhesive surface 106 or layer may be a medical-grade adhesive and can be either diaphoretic or nondiaphoretic, depending upon the particular application. The lower adhesive surface 106 may have additional types of medical adhesives laminated thereto. In some embodiments, the lower adhesive layer 106 comprises an antibacterial or anti-microbial material. For example, the lower adhesive layer may comprise one or more oligodynamic metal salts or oxides, or a combination of salts and oxides. In some embodiments, the lower adhesive layer 106 comprises a silver material, for example a silver salt, colloid, or complex. The adhesive layer 106 may be a solid layer or may be configured as an intermittent layer such as in a pattern of spots or strips. The lower adhesive layer 106 can be applied to the anchor pad 102 during manufacture, and may be further covered with a release liner 104.

The upper surface 103 may comprise a foam (e.g., closed-cell polyethylene foam) or woven material (e.g., tricot) layer. A surface of the foam or woven material layer can constitute the upper surface 103 of the anchor pad 102. In the alternative, the upper surface 103 may comprise an upper paper or other nonwoven cloth layer, and an inner foam layer may be placed between the upper surface 103 and lower adhesive layer 106.

A removable release liner 104 may cover the lower adhesive layer 106 before use. The release liner 104 may resist tearing and be divided into a plurality of pieces to assist removal of the release liner and ease attachment of the anchor pad 102 to a patient's skin. The release liner 104 may be divided into two adjacent pieces. The liner 104 may be made of a paper, plastic, polyester, or similar material. For example, the release liner 104 may comprise a material made of polycoated, siliconized paper, or another suitable material such as high density polyethylene, polypropylene, polyolefin, or silicon coated paper.

Securement Device

With reference now to FIGS. 3-8, the securement device 110 includes a first channel or lumen 120 defined between an inlet port 122 and an outlet port 124. The securement device 110 also includes at least a second channel or lumen 130. The second channel 130 connects to the first channel 120 between the inlet port 122 and the outlet port 124. The second channel 130 can also include an inlet port 132 that is disposed at an opposite end of the channel than the interconnection with the first channel 120. Those of skill in the art will appreciate that the ports 122, 124, 132 may be configured as inlet ports and/or outlet ports depending upon the application of the securement device 110.

In some embodiments, the first channel 120 is perpendicular to the second channel 130 and in other embodiments, the first and second channels intersect to form obtuse or acute angles therebetween. In one embodiment, the first channel 120 extends at an angle of between about 5° and about 30° to a bottom planar surface 114 of the securement device 110 to facilitate the insertion of a connected catheter to a patient at a desired angle, for example, 7°.

The outlet port 124 of the first channel 120 is configured to engage the distal end of a hub of a catheter or another connector. The inlet port 122 of the first channel 120 can include a male luer-lock connection fitting and a spin nut configured to connect to a medical line or a female luer-lock connection of another medical article, for example, an extension set. Similarly, the inlet port 132 of the second channel 130 can include a male luer-lock connection fitting and a spin nut configured to connect to a medical line or a female luer-lock connection of another medical article.

In some embodiments, the outlet port 124 is connected to an intravenous catheter and the inlet ports 122, 132 are connected to separate medical lines. Such a configuration advantageously provides for the fluid connection of two or more channels for introduction of two or more fluids into the body of a patient. For example, a first medical line can be fluidly coupled to inlet port 122 in order to introduce a first fluid to a patient through a catheter and a second medical line can be fluidly coupled to inlet port 132 in order to introduce a second fluid to the patient through the same catheter. In another example, the interconnection or plenum of the first and second channels 120, 130 provides for the infusion of fluid through a first inlet port 122 and aspiration and/or flushing through a second inlet port 132. In other embodiments, a catheter is connected to outlet port 124, a medical line is connected to inlet port 122, and inlet port 132 is unused or capped.

In some embodiments, the securement device 110 can include one or more valves, membranes, or septums. For example, the first channel 120 and/or second channel 130 can optionally include one or more integral one-way valves to permit the passage of fluid therethrough in a single direction, for example, in a direction toward the patient. The inlet ports 122, 132 can also optionally include needle stick membranes or septums configured to allow a syringe needle to penetrate through the membrane and into the respective channels 120, 130. For example, one or more fluids can enter the interconnection or plenum formed in the securement device 110 via a needle stick membrane and can subsequently be introduced into a patient through an intravenous catheter fluidly connected to the outlet port 124.

Figure 4:
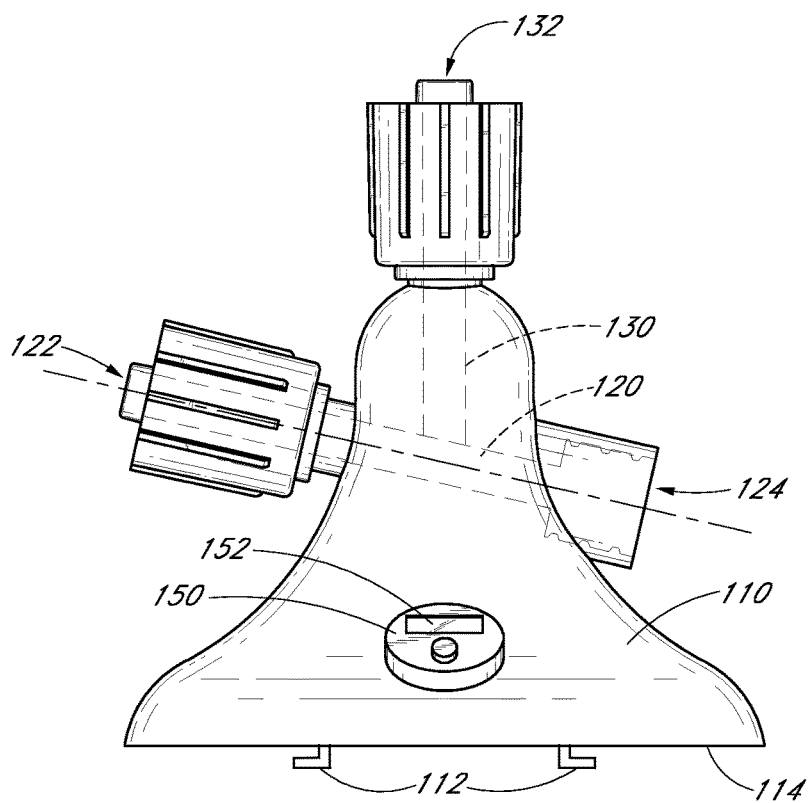
FIG. 4 is a side view of the securement device of FIG. 3.
Figure 5:
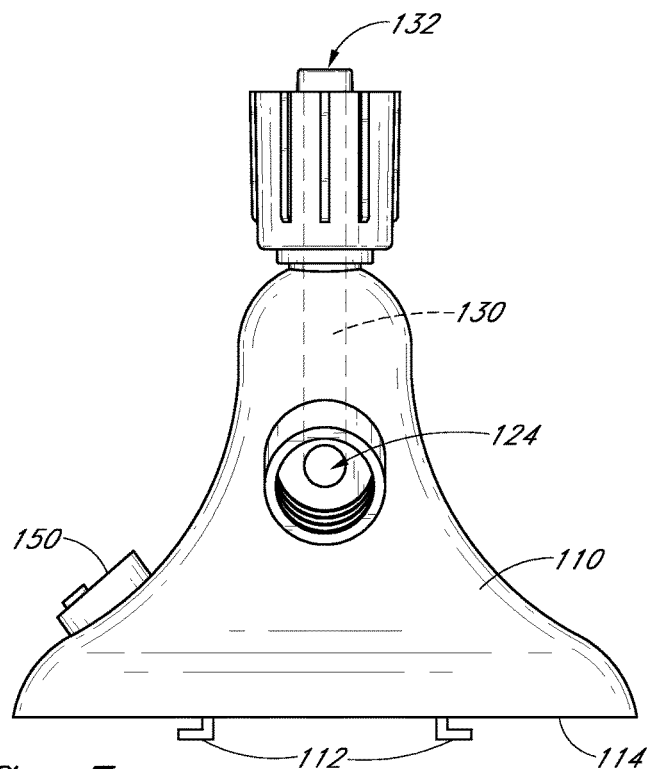
FIG. 5 is a front view of the securement device of FIG. 3.
Figure 6:
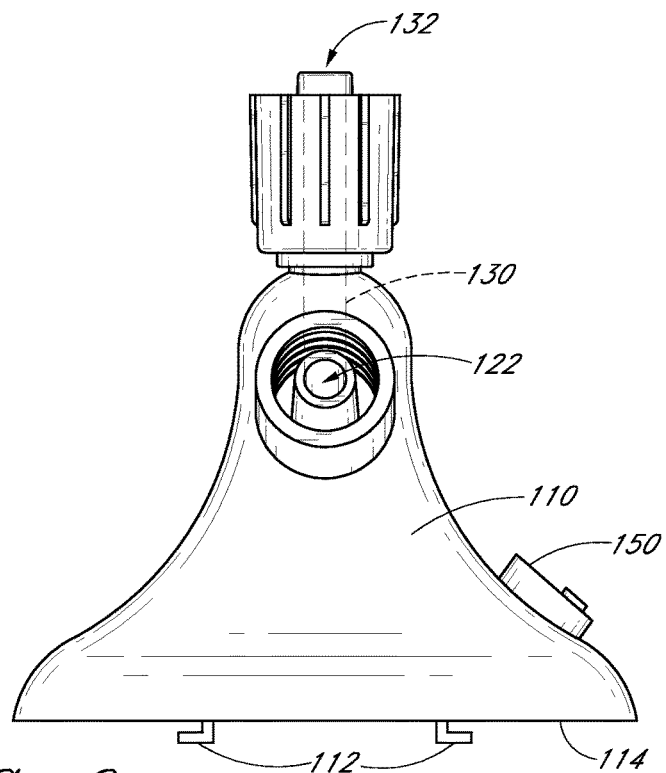
FIG. 6 is a rear view of the securement device of FIG. 3.
Figure 7:
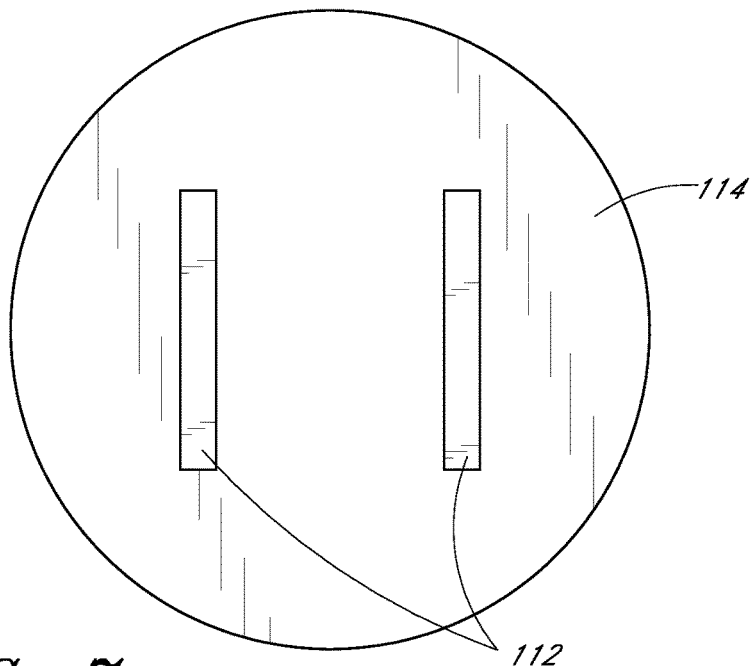
FIG. 7 is a bottom plan view of the securement device of FIG. 3.
Figure 8:
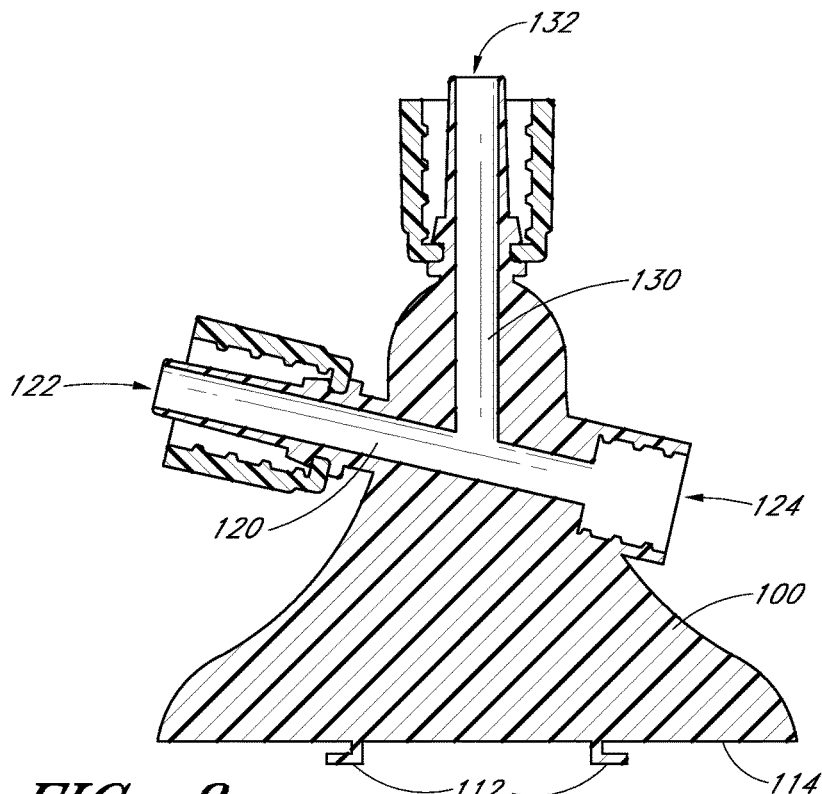
FIG. 8 is a cross-sectional view of the securement device of FIG. 3 taken along line 8-8.

The body of the securement device 110 can comprise various shapes configured to house an interconnection of the first and second channels 120, 130. For example, the body of the securement device 110 can be substantially bell shaped with a generally planar bottom surface 114 as illustrated in FIG. 4. Such a shape may be pleasing to the eye and provide an ergonomic gripping configuration to allow a healthcare provider to easily manipulate the securement device 110 and a corresponding catheterization system. Further, the base of such a shape may provide for firm support and stability when the securement device 110 is disposed on an anchor pad 102 as discussed in further detail below. Those having skill in the art will appreciate that the body of the securement device 110 can comprise other shapes, for example, the body can be generally cylindrical, conical, frustoconical, or any other suitable three dimensional shape. The body of the securement device 110 can comprise various materials, for example, hard plastics, rubbers, foams, and/or composites.

As shown in FIGS. 4-8, the securement device 110 includes structure for releasably engaging with the anchor pad 102. For example, the illustrated embodiment includes guiderails 112 extending downwardly from the bottom surface 114 of the securement device 110. Of course a single guiderail, such a T-shaped guiderail, could also be used.

The guiderails 112 can comprise various shapes that are complimentary to corresponding grooves or tracks in the anchor pad 102. For example, the securement device 110 can include two substantially L-shaped rails that are each configured to be received within, and slidably engage, a groove 109 in the anchor pad 102. In this way, the guiderails 112 releasably couple the securement device 110 to the anchor pad 102 while permitting the securement device 110 to slide or translate in at least two directions relative to the anchor pad 102. As discussed above with reference to FIG. 2, in some embodiments sliding of the securement device 110 relative to the anchor pad 102 may be prevented by one or more abutment surfaces 107.

The securement system 100 can optionally include one or more timers 150 so as to be accessible by the healthcare provider. In some embodiments, the timer 150 is disposed on an outer surface of the securement device 110 and optionally includes a display 152.

The timer 150 may be configured to measure elapsed time and can be activated manually by a user, remotely by a user, and/or by a triggering event, for example, the connection of one or more medical articles to the securement device 110 and/or the passage of fluid through a lumen in the securement device 110. The timer 150 indicates a time-based characteristic of the medical article or line, such as, for example, the length of time the medical article or line has been in place on the patient. In some implementations, the timer 150 measures a flow rate of fluid into the patient and compares the measured flow rate to a target flow rate. Thus, the timer 150 may be used to verify that the lumens of the medical lines, securement device, and/or catheter are not occluded or partially occluded.

The timer 150 can be flexible or rigid, and can be disposed directly on the securement device 110. In some embodiments, the timer 150 is disposed on the anchor pad 102. By prominently positioning the timer 150, the timer can provide an easy-to-use and reliable visual indicator of elapsed time. The timer 150 can be a battery-operated timer or a chemically-active timer. Embodiments of a chemically active timer 150 can change color or provide another visual response when exposed to air or a selected chemical for a given length of time.

In some implementations, the timer 150 is activated by a healthcare provider at generally the same time a catheter is connected to the outlet port 124 (or just prior to or just after insertion). The activated timer 150 may then provide a visual indication of the length of time elapsed or period since the catheter was connected to the securement device 110. The timer 150 may provide, in addition to or instead of a visual response, an audible indication or alarm of a given length of time. For example, the timer 150 may beep, chirp, or otherwise emit sound indicative of a time-based characteristic.

The period between indication outputs from the timer 150 can be fixed or variable. For example, the timer 150 can provide an indication after a first time period and then provide a second indication after a second time period. The first and second time periods may have the same or different durations. The first indication may be the same or different than the second indication. For example, the timer 150 can provided an audible indication after the first time period and a visual indication after the second time period. Thus, the timer 150 can be used to signal when the medical line should be replaced and/or re-sited.

The securement device 110 can optionally include one or more pressure sensors or transducers configured to measure the pressure of an infusate flowing through the securement device 110. For example, the securement device 110 can include a pressure sensor coupled with the inlet or outlet ports 122, 132, 124 to measure the pressure of flowing fluid. In some embodiments, a pressure transducer provides an audible or visual indication or alarm when the pressure of the infusate exceeds a given threshold or is below a given threshold. For example, a pressure transducer may be configured to provide an audible alarm when pressure changes as a function of infiltration or extravasation. A spike or increase in the sensed pressure may indicate that the vein has been infiltrated.

The securement device 110 can optionally include one or more flow sensors or meters configured to sense a rate of fluid flow through the first channel 120 and/or second channel 130. For example, the securement device 110 can include a flow sensor coupled with the outlet port 124 to measure a rate of infusate flow therethrough. The one or more flow sensors can be configured to provide an audible or visual indication or alarm when a flow rate through the first channel 120 and/or second channel 130 exceeds a given threshold or is below a given threshold. For example, a flow sensor can be configured to provide an audible alarm when a flow rate through the connection device 110 is below a certain threshold such that the patient is not receiving sufficient fluid or infusate delivery.

The optional timers, pressure transducers, and/or flow sensors can include stored memory elements including one or more libraries of stored settings. For example, drug or medication libraries with stored settings relating to each individual drug or medication can be stored on memory elements to provide threshold values to the optional timers, pressure transducers, and/or flow sensors. In some embodiments, such memory elements can be configured to trigger an audible or visual indication or alarm when a given dosage has been met and/or when a pressure or flow characteristic of a given infusate deviates from an expected value.

Method of Use

The following discussion of the method of use will be with reference to FIGS. 9-12, and will be in the context of intravenous catheterization. As the following discussion will illustrate, however, it is understood that the securement system 100 can be used in other medical procedures as well. The discussion of the method of use is intended to augment the above description, and, thus, should be read together.

A healthcare provider typically begins the catheterization process by positioning the catheter hub 202 at a desired location above a vein. The healthcare provider introduces a needle or other stylus through a cannula portion of the catheter hub 202 and into the skin of the patient at a desired incident angle. For intravenous use, the catheter hub 202 commonly has an incident angle of approximately 7°. The healthcare provider then inserts the cannula of the catheter hub 202 into the patient and withdraws the needle or stylus. Part of the catheter hub 202 remains exposed above the skin. The healthcare provider can then connect the distal end of the catheter hub 202 to the outlet port 124 of the securement device 110. In some embodiments, the outlet port 124 can include internal threads to allow the hub 202 to be threadably secured to the outlet port 124. As discussed above, upon introducing the catheter into the patient's vein, the timer 150 may be manually, automatically, and/or remotely activated to measure an elapsed time. In some embodiments, the timer 150 may be activated upon connection of the catheter hub 202 to the securement device 110 or upon connection of a medical line to the catheter hub 202 via the securement device 110.

Figure 11:
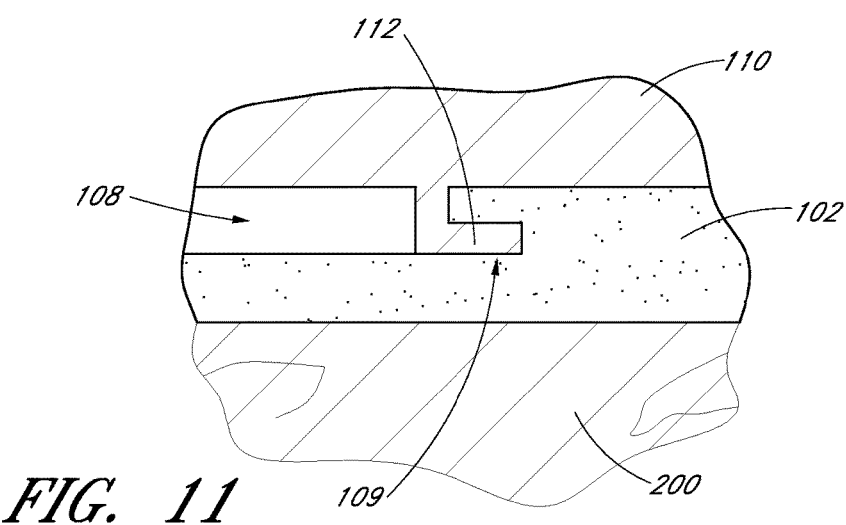
FIG. 11 is a close-up view of the guiderails of the securement device slidably engaged with the grooves of the anchor pad from FIG. 10.
Figure 12:
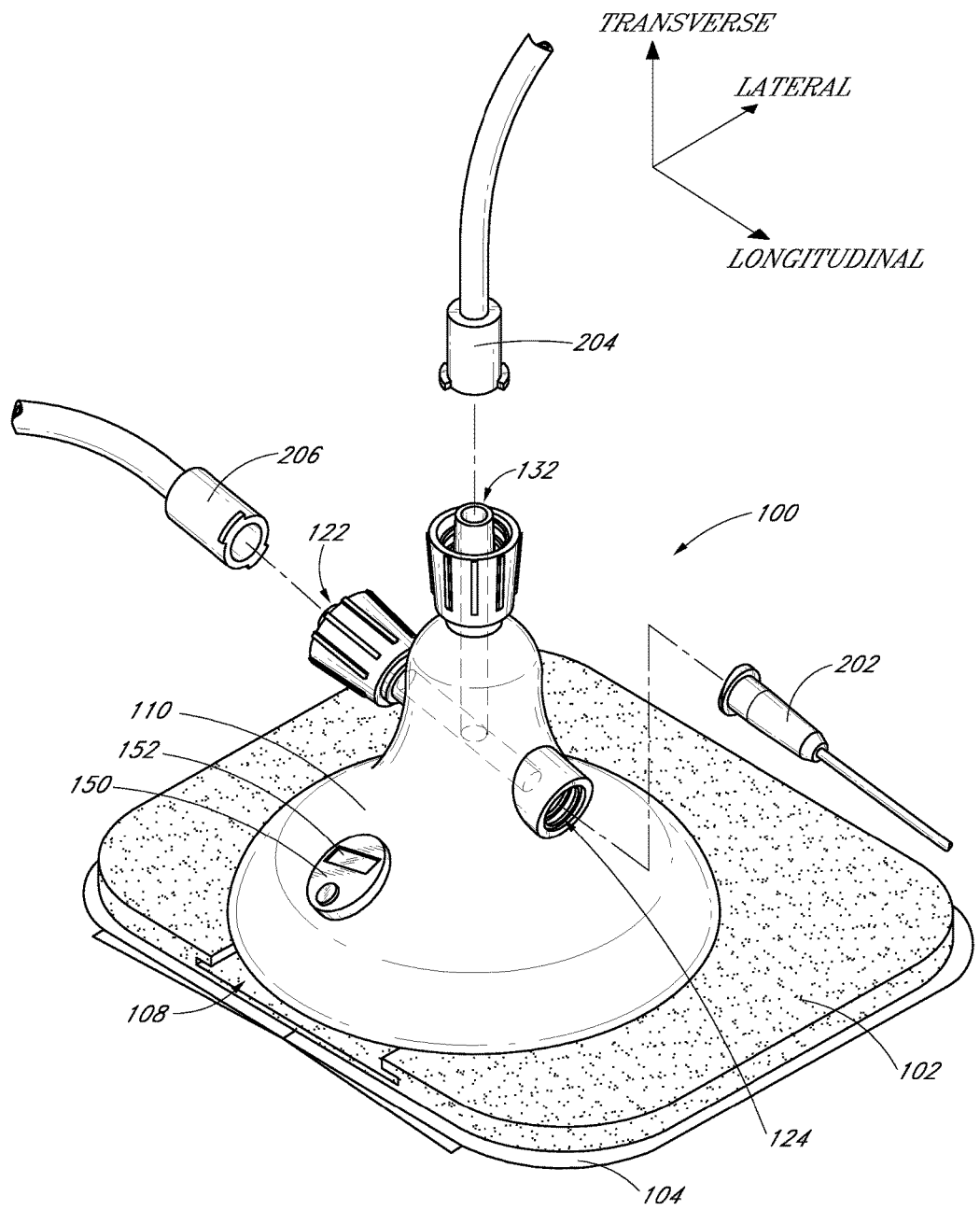
FIG. 12 is an exploded perspective view of the securement system of FIG. 1 schematically depicted as attaching to two medical lines and an intravenous catheter.

With the securement device 110 and the catheter hub 202 connected to one another, the healthcare provider may next align the guiderails 112 of the securement device 110 with the grooves 109 in the recess 108 of the anchor pad 102. With the guiderails 112 aligned with the grooves 109, the healthcare provider slides the securement device 110 relative to the anchor pad 102 to secure the securement device 110 to the anchor pad 102 via the engagement between the grooves 109 and the guiderails 112. As shown in FIG. 11, the complimentary shapes of the guiderails 112 and the grooves 109 may inhibit transverse and longitudinal movement of the securement device 110 relative to the anchor pad 102 when the securement device 110 is slidably engaged with the anchor pad 102. Lateral sliding movement of the securement device 110 relative to the anchor pad 102 may be limited in at least one direction by one or more abutment surfaces of the anchor pad 102 as discussed above.

Before or after the securement device 110 is slidably engaged with, and releasably secured to, the anchor pad 102, the healthcare provider removes the releasable liner 104 which initially covers the adhesive lower layer of the anchor pad 102. The healthcare provider attaches the pad 102 to the patient's skin proximate to the indwelling catheter. The healthcare provider positions the anchor pad 102 over the placement site and places the exposed bottom layer against the patient's skin 200 so as to adhere the anchor pad 102 to the patient. Light pressure over the anchor pad 102 and/or securement device 110 assures good adhesion between the anchor pad 102 and the patient's skin 200. The anchor pad 102, due to its flexibility, conforms to the contours of the patient's skin. Additionally, the anchor pad 102 can be attached to the patient before the securement device 110 is secured to the anchor pad 102. With the securement device 110 and the anchor pad 102 slidably engaged with one another, and the anchor pad 102 adhered to the patient's skin 200, movement of the catheter 202 may be limited in at least the longitudinal direction.

The healthcare provider may then connect additional medical articles to the securement device 110. For example, the healthcare provider may connect a primary medical line 206 to inlet port 122 to establish a fluid connection between the catheter hub 202 and the medical line 206. The healthcare provider may optionally connect a secondary medical line 204 to inlet port 132 to fluidly connect the medical line 204 to the catheter hub 202 via the securement device 110. Alternatively, the inlet port 132 may be used to aspirate or flush the catheter hub 202, medical line 206, or securement device 110. In this way, the components of catheterization system including the catheter hub 202 and the medical lines 204, 206 can be fluidly interconnected by the securement device 110 and the resultant interconnection can be secured relative to the patient's skin 200 by the securement device 110 and the anchor pad 102.

In some embodiments, the healthcare provider may dispose a sterile dressing over the insertion site and at least a portion of the catheter hub 202. The optional dressing can be attached to and/or integrated with the anchor pad 102 or securement device 110. The dressing can be configured to fold, bend, or rotate down over the insertion site area.

The present securement systems thus provide a sterile, needle-, and tape-free way to fluidly connect components of a catheterization system and to secure the interconnection to patient. These systems eliminate the use of tape, and if prior protocol required suturing, they also eliminate accidental needle sticks, suture-wound-site infections and scarring. In addition, the systems can be configured to be used with any of a wide variety of catheters, fittings, tubes, wires, and other medical articles. Patient comfort is also enhanced and application time is decreased with the use of the present securement systems.

It is to be noted that the figures provided herein are not drawn to any particular proportion or scale, and that many variations can be made to the illustrated embodiments. Those of skill in the art will recognize that the disclosed aspects and features shown herein are not limited to any particular embodiment of a stabilization system, and stabilization systems that include one or more of the features herein described can be designed for use with a variety of medical articles.

The various embodiments of the securement systems described above in accordance with the present invention thus provide a means to releasably secure a connector fitting or extension set to a patient. An insertion site of a catheter attached to the connector fitting or extension set may be covered with an integrated dressing.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. In addition to the variations described herein, other known equivalents for each feature can be mixed and matched by one of ordinary skill in this art to construct stabilization systems and techniques in accordance with principles of the present invention.

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A medical article securement system comprising:
   a retainer defining a first lumen between a first port and a second port, and a second lumen fluidly connected to the first lumen;
   an anchor pad having an upper surface and a lower surface, at least a portion of the lower surface being covered by adhesive;
   interengaging structure releasably securing the retainer to the anchor pad; and
   a timer configured to be activated by fluid flow through the retainer.

2. The system of claim 1, further comprising a recess disposed on one of the retainer and the anchor pad.

3. The system of claim 2, further comprising at least one guiderail configured to engage with the recess.

4. The system of claim 3, wherein the at least one guiderail is disposed on one of the retainer and the anchor pad, and the recess is disposed on the other of the retainer and the anchor pad.

5. The system of claim 3, wherein the recess comprises a groove configured to receive at least a portion of the at least one guiderail.

6. The system of claim 5, wherein the groove has a shape that is complimentary to the at least one guiderail.

7. The system of claim 5, wherein the retainer slidably engages the anchor pad at least when the at least one guiderail is received within the groove.

8. The system of claim 1, wherein the timer is chemically activated.

9. The system of claim 1, further comprising a pressure sensor configured to measure a pressure of fluid that flows through the retainer.

10. The system of claim 9, wherein the pressure sensor is configured to indicate when the measured pressure exceeds a threshold value.

11. The system of claim 1, further comprising a flow sensor configured to measure a flow rate through the retainer.

12. The system of claim 1, wherein the retainer comprises a valve.

13. The system of claim 1, wherein the first lumen extends at an angle of between 5° and 30° relative to the upper surface of the anchor pad when the retainer is releasably secured to the anchor pad.

14. A medical article securement system comprising:
a retainer defining a first lumen between a first port and a second port, and a second lumen fluidly connected to the first lumen;
an anchor pad having an upper surface and a lower surface, at least a portion of the lower surface being covered by adhesive;
interengaging structure releasably securing the retainer to the anchor pad; and
a timer configured to be activated by connecting a medical article to the retainer.

15. The system of claim 1, further comprising a recess disposed on one of the retainer and the anchor pad.

16. The system of claim 15, further comprising at least one guiderail configured to engage with the recess.

17. The system of claim 16, wherein the recess comprises a groove configured to receive at least a portion of the at least one guiderail.

18. The system of claim 17, wherein the groove has a shape that is complimentary to the at least one guiderail.

19. The system of claim 18, wherein the retainer slidably engages the anchor pad at least when the at least one guiderail is received within the groove.

20. The system of claim 14, wherein the timer is chemically activated.

21. The system of claim 14, further comprising a pressure sensor configured to measure a pressure of fluid that flows through the retainer.

22. The system of claim 21, wherein the pressure sensor is configured to indicate when the measured pressure exceeds a threshold value.

23. The system of claim 14, further comprising a flow sensor configured to measure a flow rate through the retainer.

24. The system of claim 14, wherein the retainer comprises a valve.

25. The system of claim 14, wherein the first lumen extends at an angle of between 5° and 30° relative to the upper surface of the anchor pad when the retainer is releasably secured to the anchor pad.

* * * * *